US012778418B2

(12) United States Patent
Ciardo et al.

(10) Patent No.: US 12,778,418 B2
(45) Date of Patent: Nov. 3, 2026

(54) DEVICE AND METHOD FOR DETECTING THE OCULAR FUNDUS REFLEX

(71) Applicant: OCUMETRICA S.R.L, Padua (IT)

(72) Inventors: Marco Ciardo, Padua (IT); Nicola Riste', Jesi (IT); Stefano Piermarocchi, Padua (IT)

(73) Assignee: OCUMETRICA S.R.L, Padua (IT)

( * ) Notice: Subject to any disclaimer, the term of this patent is extended or adjusted under 35 U.S.C. 154(b) by 243 days.

(21) Appl. No.: 18/555,492

(22) PCT Filed: Apr. 15, 2022

(86) PCT No.: PCT/IB2022/053557
§ 371 (c)(1),
(2) Date: Oct. 13, 2023

(87) PCT Pub. No.: WO2022/219596
PCT Pub. Date: Oct. 20, 2022

(65) Prior Publication Data

US 2024/0188821 A1 Jun. 13, 2024

(30) Foreign Application Priority Data

Apr. 16, 2021 (IT) ........................ 102021000009587

(51) Int. Cl.
*A61B 3/12* (2006.01)
*A61B 3/00* (2006.01)
(Continued)

(52) U.S. Cl.
CPC .............. *A61B 3/12* (2013.01); *A61B 3/0025* (2013.01); *A61B 3/113* (2013.01); *G06T 7/00* (2013.01); *G06T 2207/30041* (2013.01)

(58) Field of Classification Search
CPC ......... A61B 3/0025; A61B 3/113; A61B 3/12; G06T 7/00; G06T 2207/30041
See application file for complete search history.

(56) References Cited

U.S. PATENT DOCUMENTS 10,602,926 B2 3/2020 Wang
2002/0089643 A1 7/2002 Ogawa
(Continued)

OTHER PUBLICATIONS

International Search Report for PCT/IB2022/053557 dated Jul. 27, 2022, 3 pages.
(Continued)

*Primary Examiner* — Jack Dinh
(74) *Attorney, Agent, or Firm* — NIXON & VANDERHYE

(57) ABSTRACT

Device for detecting the ocular fundus reflex, which comprises an optical detector (2), which detects images of a person's face, and an optical emitter (3), which is operable to project a beam of electromagnetic rays onto the person's eyes. The device also comprises an electronic processing system (5) connected to the optical detector (2) and the optical emitter (3). The electronic processing system (5) is provided with a face tracking module, which determines the position of the person's face, and with an eye state detection module, which calculates both the gaze direction on the basis of light points (PL) and a state parameter (PS) representative of the degree of eye opening and compares this state parameter (PS) with a threshold value (VS). If the aforesaid state parameter (PS) is higher than the threshold value (VS), the processing electronic system (5) switches the optical emitter (3) into an operational state for a determined time interval (IT), in which the optical emitter (3) projects a beam of electromagnetic rays onto the person's eyes, which generate a corresponding beam of reflected rays of the ocular fundus. During the aforesaid time interval (IT), the optical detector (2) acquires analysis images containing the beam of reflected rays of the ocular fundus, so that the latter can be analysed to assess possible abnormalities.

10 Claims, 6 Drawing Sheets

(51) Int. Cl.
*A61B 3/113* (2006.01)
*G06T 7/00* (2017.01)

(56) References Cited

U.S. PATENT DOCUMENTS

| | | | |
|---|---|---|---|
| 2009/0180073 | A1 | 7/2009 | Ichikawa et al. |
| 2016/0048735 | A1 | 2/2016 | Ohya |

OTHER PUBLICATIONS

Written Opinion of the ISA for PCT/IB2022/053557 dated Jul. 27, 2022, 6 pages.

Italian Search Report for IT 2021000009587, dated Dec. 22, 2021, 10 pages.

DEVICE AND METHOD FOR DETECTING THE OCULAR FUNDUS REFLEX

CROSS-REFERENCE TO RELATED APPLICATIONS

This application is the U.S. national phase of International Application No. PCT/IB2022/053557filed Apr. 15, 2022 which designated the U.S. and claims priority to IT 102021000009587 filed Apr. 16, 2021, the entire contents of each of which are hereby incorporated by reference.

FIELD OF THE INVENTION

The present invention relates to a device and a method for detecting the ocular fundus reflex, according to the preamble of the corresponding independent claims.

The device and the method in question are part of the production of instrumentations used in the ophthalmological field, in particular in neonatal and infant ophthalmology, in order to analyse a patient's eyesight.

In particular, the device and the method dealt with can be advantageously used to acquire images of the ocular fundus in order to detect any abnormalities of the ocular fundus reflex which are indicative of the presence of possible issues or diseases and/or the need to perform more in-depth examinations of the patient.

Suitably, the device and the method in question are particularly (although not exclusively) suitable for use in newborn or child patients or, in general, in patients who are not able to actively collaborate with the doctor in performing the examination.

STATE OF THE ART

Blindness and ophthalmological diseases in childhood are a serious medical and social issue worldwide, with an even higher incidence in less economically advanced countries. In fact, it is estimated that about % of cases of childhood blindness affect Asian and African countries, but the issue is also present and significant in more economically advanced countries. For example, in the United States alone, it is estimated that vision loss and vision disorders in children have an economic impact of approximately $6 billion per year.

In the field of neonatal ophthalmology, it is therefore particularly felt the need for early diagnosis (already in the first days of a newborn's life) to detect potential issues with the child's visual system, in order to be able to treat or prevent diseases that could cause blindness or severe low vision (such as congenital cataracts, corneal opacity, retinopathy of prematurity, etc.), or even put the child's life at risk (such as retinoblastoma).

In pediatrics, an examination to which the child is subjected, in order to identify early possible issues of the visual system, is the so-called red reflex test.

The red reflex test is conventionally carried out by a doctor (in particular a pediatrician or an ophthalmologist), for example using an ophthalmoscope, which projects a light ray through the transparent media of the eye (cornea, crystalline lens, vitreous) as far as the ocular fundus (retina) which generates a red coloured reflected ray. This reflected ray propagates backwards, passing again through the transparent media of the eye until it reaches the opening of the ophthalmoscope, allowing the doctor to examine this reflected ray. The presence of abnormalities in the reflected ray (such as dark spots, markedly decreased intensity, the presence of a white reflex, lack of homogeneity of the reflex, etc.) are an indication to the doctor of possible issues with the state of the eye, requiring the child to undergo eye examinations or more in-depth tests.

However, this red reflex test is often not easy to perform on children, particularly newborns.

In fact, the newborn or the infant is not able to cooperate actively with the doctor in order to place and keep the eyes open in the correct position in front of the ophthalmoscope, as the child often tends to move his head and keep his eyes closed, particularly when stimulated by visible light.

This not only requires the presence and intervention of the doctor during the performance of the test, but also makes it difficult and potentially time-consuming the performance thereof. In fact, the light ray projected by the ophthalmoscope tends to dazzle the child, who instinctively closes his eyes, preventing the reflected ray from being detected. Also, even with open eye, the light ray causes miosis (a pupil constriction), making it more difficult or impossible to detect the reflected ray. In these cases it is necessary to administer eye drops that dilate the pupil, blocking the cholinergic receptors, often with non-negligible systemic effects.

Ophthalmoscopic devices are known in the state of the art which, in order to perform eye examinations, involve projecting an infrared ray into the eye and detecting the corresponding reflex thereof (in this case, with a black and white camera it appears white in colour), to identify possible abnormalities indicative of vision issues. As infrared rays are not perceived by the patient, they do not cause glare and do not cause pupil constriction, making it easier to perform the examination.

For example, U.S. Pat. No. 10,602,926 discloses a device of a known type for automatically acquiring retinal reflex images, which comprises a light source (such as an LED) set up to project a ray of infrared light onto the patient's eyes, and a camera for detecting a series of images of the patient's face. In particular, this device uses an eye tracking algorithm to command the camera to acquire an image when the patient is looking at its axis, in order to detect an image in which the eye fundus reflex is present.

However, this latter device of known type is also not particularly suitable for use in children, particularly infants, since in fact an active cooperation of the patient is nevertheless required for the performance of the examination.

In particular, even with this device of known type, the doctor finds it particularly difficult to keep the child's head in the correct position and the eyes open in order to allow the instrument to acquire the images suitable for analysing the ocular fundus reflex.

SUMMARY OF THE INVENTION

In this situation, the essential object of the present invention is therefore to overcome the drawbacks manifested by the solutions of the known type, by providing a device and a method for detecting the ocular fundus reflex which enable the ocular fundus reflex to be acquired simply and reliably, in particular in newborn, infant or child patients.

A further object of the present invention is to provide a device and a method for detecting the ocular fundus reflex which are capable of acquiring the ocular fundus reflex in an automated manner, in particular without the need for the presence of a doctor or operator on site.

A further object of the present invention is to provide a device and a method for detecting the ocular fundus reflex which are completely safe for the patient.

A further object of the present invention is to provide a device for detecting the ocular fundus reflex which is simple to use.

A further object of the present invention is to provide a device and a method for detecting the ocular fundus reflex which do not require the use of eye drops containing medicaments potentially hazardous to the health of the child.

A further object of the present invention is to provide a device for detecting the ocular fundus reflex which is inexpensive to manufacture.

BRIEF DESCRIPTION OF THE DRAWINGS

The technical characteristics of the invention, according to the aforesaid objects, can clearly be seen in the content of the claims below, and its advantages will become more readily apparent in the detailed description below, made with reference to the accompanying drawings, which represent a purely illustrative and non-limiting embodiment, wherein:

DETAILED DESCRIPTION OF THE INVENTION

Figure 1:
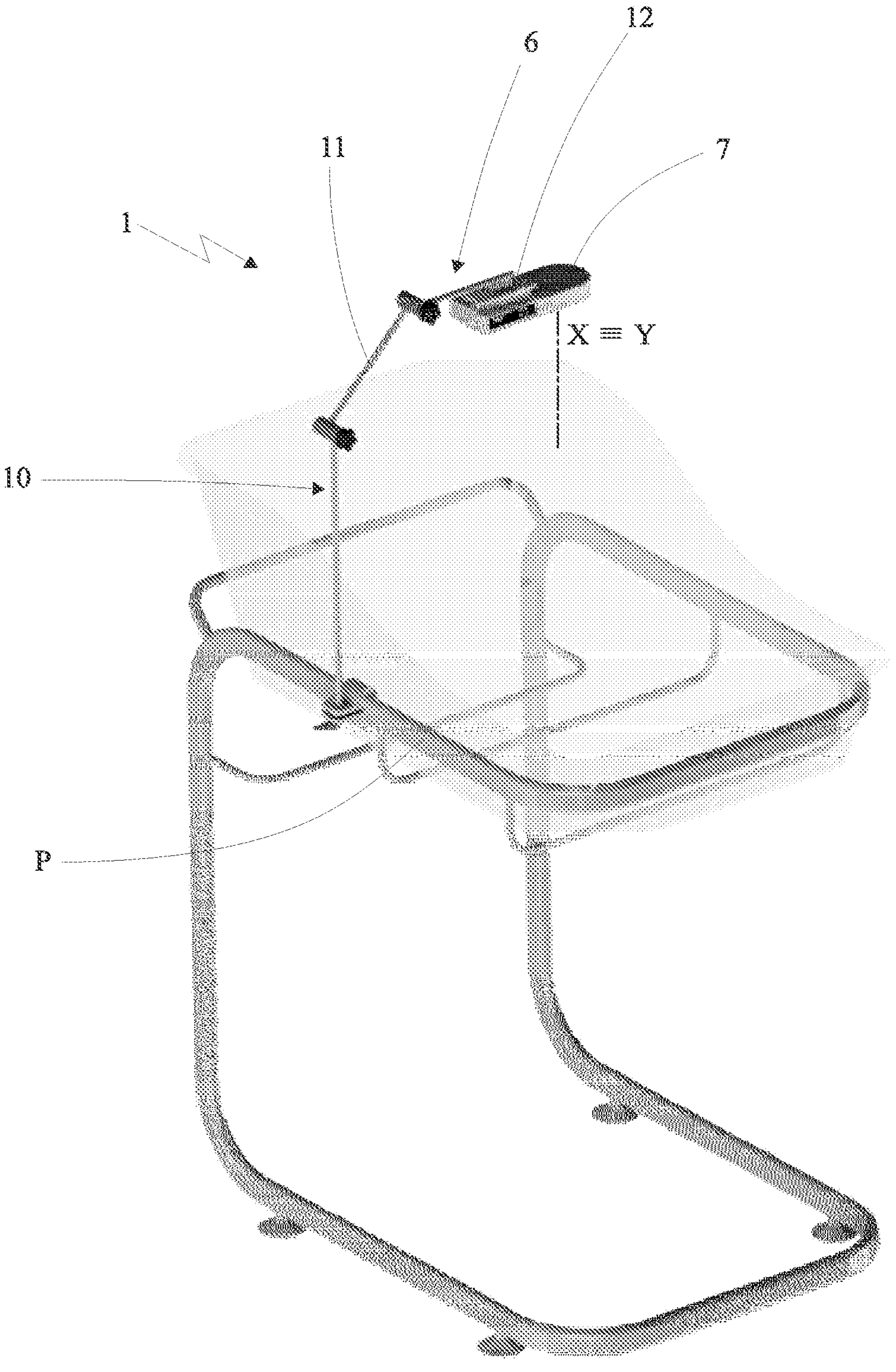
FIG. 1 illustrates a perspective view of an example of the device for detecting the ocular fundus reflex in question, in a particular application situation.
Figure 2:
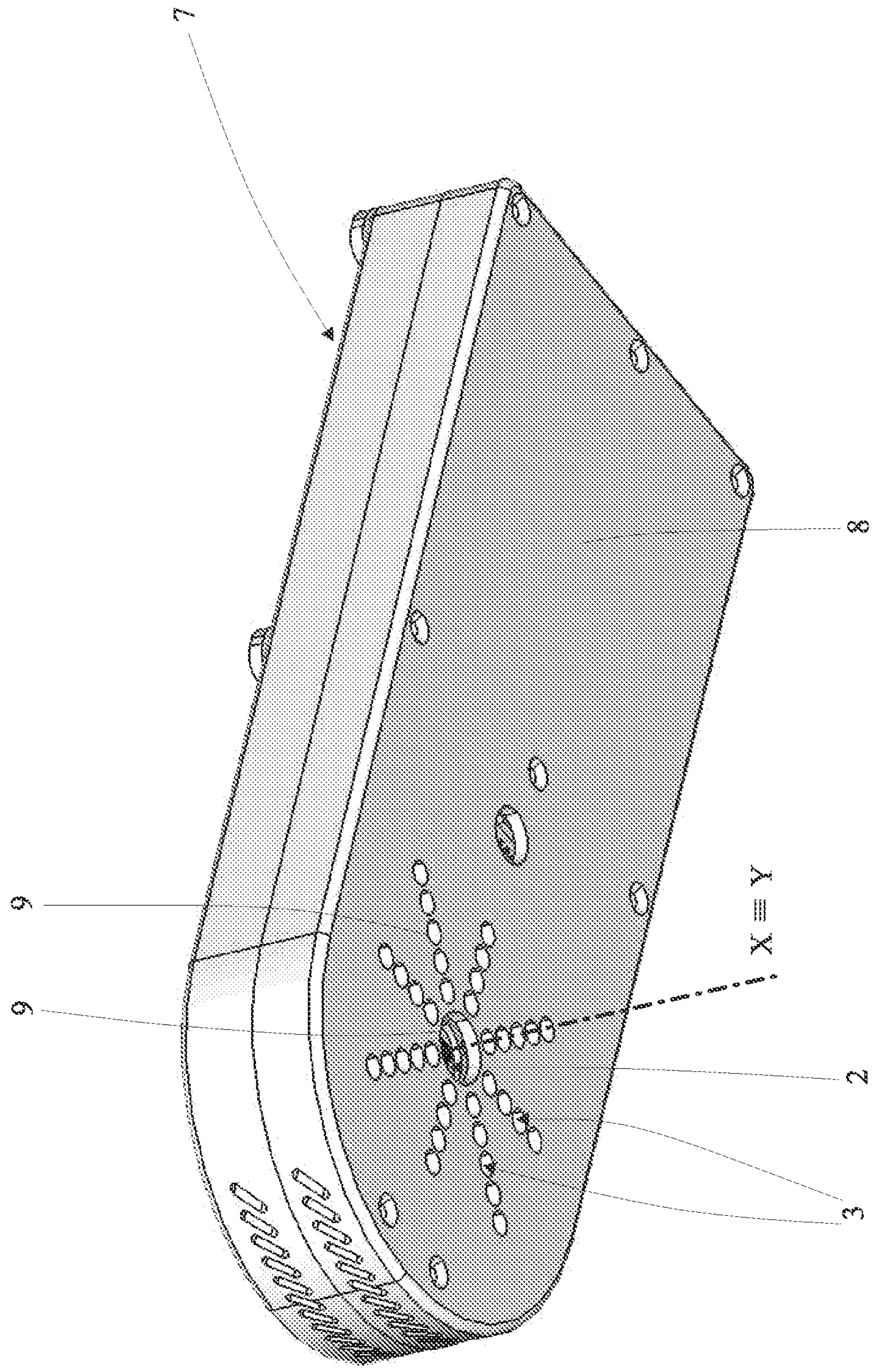
FIG. 2 illustrates a front perspective view of a detail of the device in question.

The present invention relates in the first aspect to a device (1) for detecting the ocular fundus reflex, which comprises:

- at least one optical detector (2), which is designed to detect images of a person's face;
- at least one optical emitter (3), which is designed to project at least one beam of electromagnetic rays at least on the eyes of the face of said person, which eyes are capable to generate a beam of reflected rays of the ocular fundus;
- an electronic processing system (5), which is operatively connected to said optical detector (2) to receive said images, and is operatively connected to said optical emitter (3) to switch said optical emitter (3) between an operational state, in which said optical emitter (3) is adapted to project said beam of electromagnetic rays onto the face of said person, and a non-operational state;

said device (1) being characterized in that said electronic processing system (5) is equipped with:

- a face tracking module, which is designed to calculate, from said images, a set (I) of reference points (PR) indicative of the position of the person's face in said image;
- an eye state detection module, which is designed to:
  - select, in said set (I) of reference points (PR), a subset (SI) of points of interest (PI) relative to the eye area of the face in said images;
  - identify, in said subset (SI), upper points (PIS) indicative of supraocular areas and lower points (PII) indicative of subocular areas;
    - calculate, as a function of the reciprocal position of the points of interest (PI) of said subset (SI), at least one state parameter (PS) representative of the degree of opening of the eyes of the face in said images, wherein said state parameter (PS) is calculated as a function of the distance between said upper points (PIS) and said lower points (PII);
  - compare said state parameter (PS) with at least one threshold value (VS);

with said state parameter (PS) beyond said threshold value, switch said optical emitter (3) into said operational state for a determined time interval (IT), within which said optical detector (2) is adapted to acquire analysis images containing the beam of reflected rays of the ocular fundus caused by said beam of electromagnetic rays generated by said optical emitter (3).

Referring to the accompanying drawings, a device for detecting the ocular fundus reflex, which is the subject matter of the present invention, is collectively referred to as 1.

The device 1 and the method in question are intended to be used in ophthalmology to detect the ocular fundus reflex in order to be able to assess the presence, in this reflex, of abnormalities indicative of possible pathologies or issues of the patient's eyesight and/or the need to perform in-depth eye examinations.

In particular, the device 1 and the method are particularly suitable to be used, in the paediatric field to analyse the ocular fundus reflex in children, particularly newborns and infants.

With reference to the example embodiment illustrated in the accompanying figures, the device 1 in question comprises at least one optical detector 2, which is set up to detect images of the face of a person (e.g. a child) to be examined. The device 1 and the method according to the present invention are also usable for detecting the ocular fundus reflex also in a non-human animal subject, for example in the field of veterinary medicine.

Adults who are unable to undergo standard eye examinations due to cognitive impairment or other general clinical issues are also eligible.

In one embodiment, therefore, the device 1 and the method are aimed at detecting the ocular fundus reflex in a person, i.e. a human animal subject, preferably in a child, by which expression it is meant a human being in the time interval between birth and puberty, preferably in a newborn or in an infant.

In another embodiment, the device 1 and the method are aimed at detecting the ocular fundus reflex in a non-human animal subject.

For the sake of exposure simplicity, reference will be made in this application to a person, or to subjects that are in any case humans such as children or infants, in any case it being understood that the device and the method are also usable on non-human animal subjects.

In particular, the optical detector 2 is provided with a field angle suitable for capturing at least the face of the person, depending on the distance at which it is placed from the person.

Appropriately, the optical detector 2 is provided with an optical X-axis (preferably centred with respect to the field angle) intended to be intercepted by the person (in particular by the person's face).

Advantageously, the optical detector 2 comprises a camera provided with optics defining the aforesaid optical axis X.

Preferably, the optical detector 2 (and in particular the camera) is set up to detect electromagnetic radiations in the visible and/or infrared range, depending on the applications envisaged, as specified below.

The device 1 in question further comprises an optical emitter 3, which is set up to project a beam of electromagnetic rays onto the eyes of the person to be examined.

The patient's eye, when hit by the aforesaid beam of electromagnetic rays, is likely to generate a beam of reflected rays from the ocular fundus, in a manner per se known in the medical ophthalmological field and, therefore, not dealt with here.

As described in detail below, the optical detector 2 is capable of detecting the images of the face of the person containing the beam of reflected rays in order to analyse the ocular fundus reflex.

Figure 3:
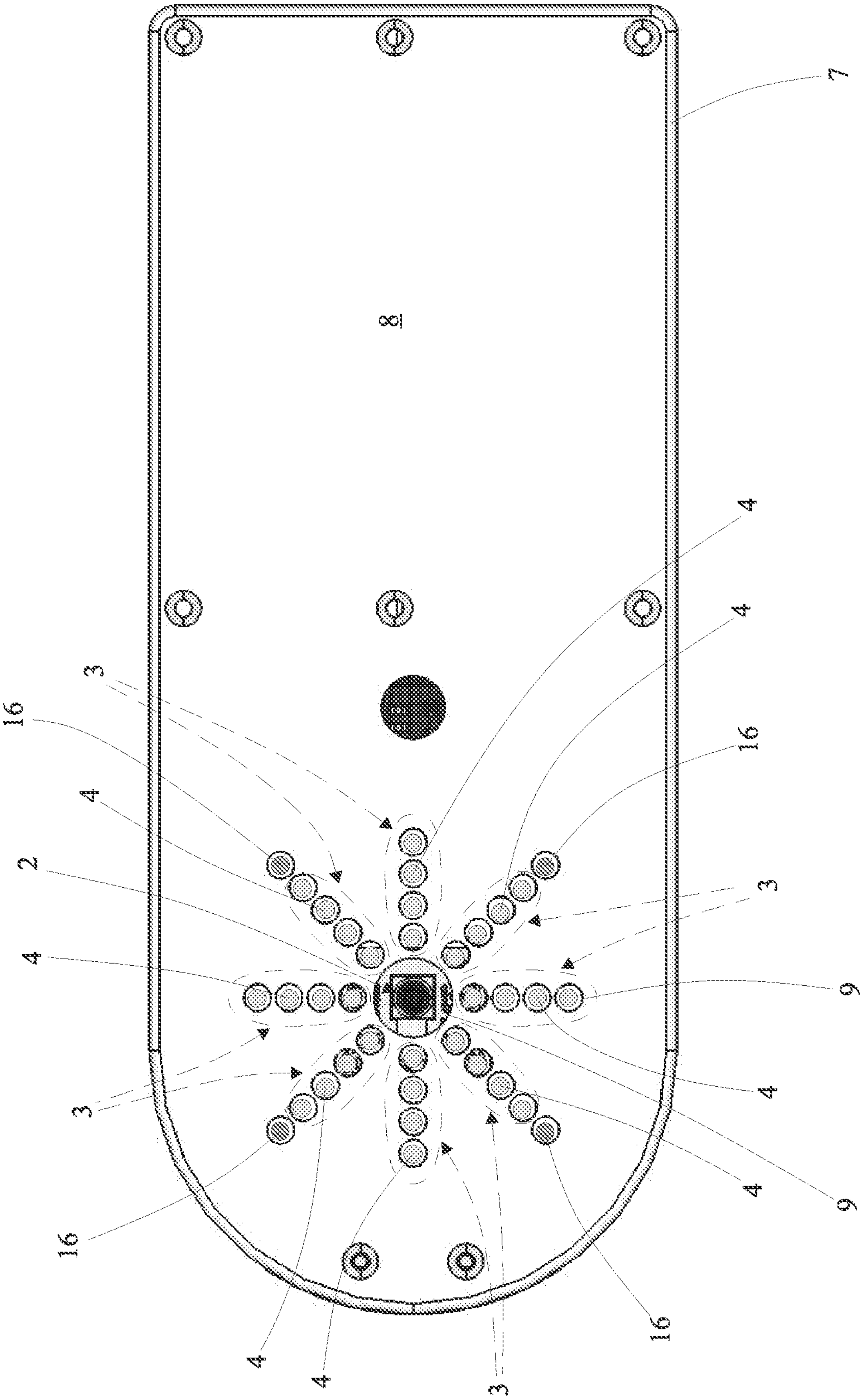
FIG. 3 shows a front plan view of the detail of the device illustrated in FIG. 2.
Figure 4:
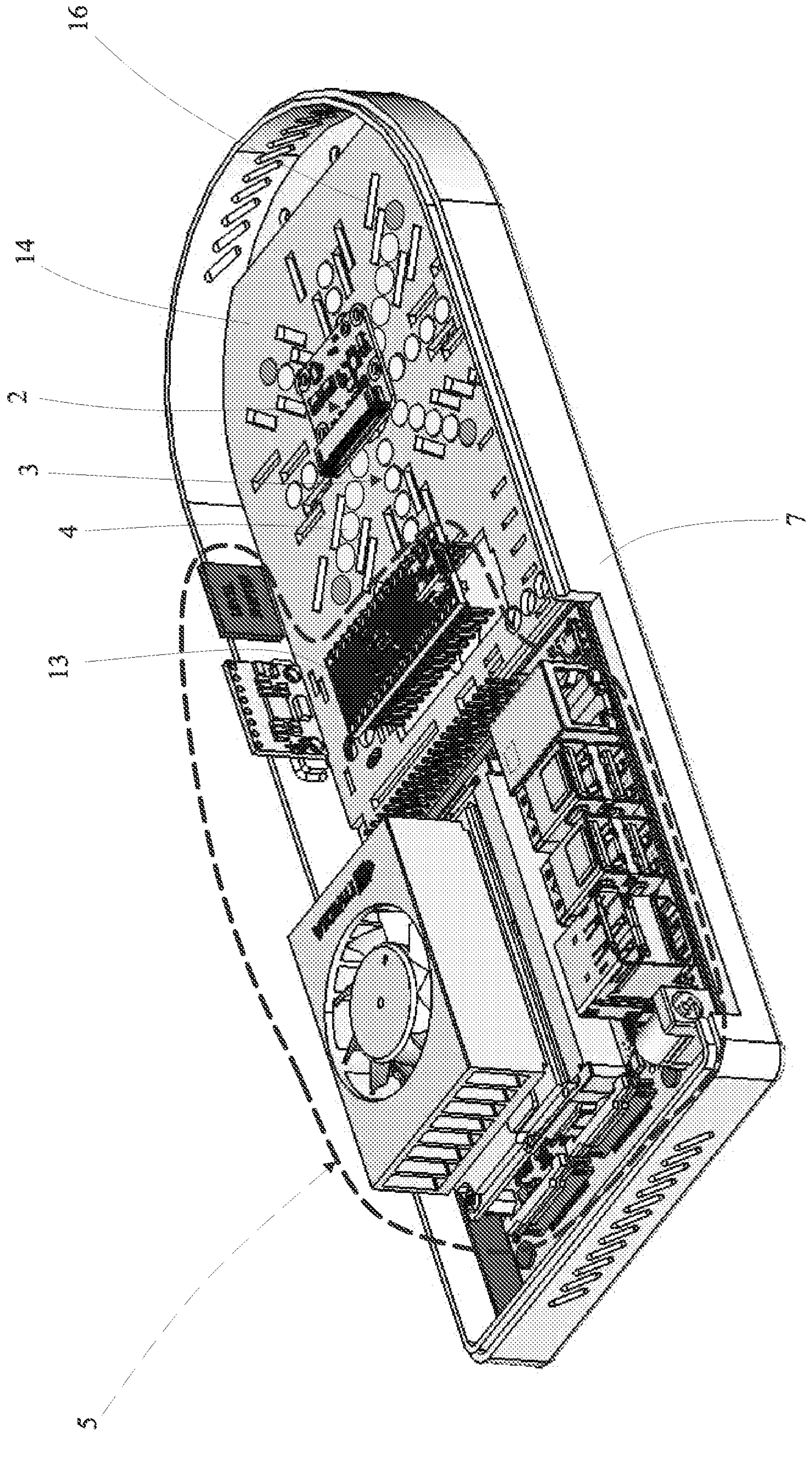
FIG. 4 shows a perspective view of the device in which some parts have been removed to better highlight some internal components of the device itself.

Advantageously, the optical emitter 3 comprises several optical sources 4, e.g. of the LED type (shown schematically in FIGS. 3 and 4).

Preferably, the optical emitter 3 (and in particular the optical sources 4) is set up to define a projection axis Y of the beam of electromagnetic rays aligned with the optical axis X of the optical detector 2.

Advantageously, the optical emitter 3 is set up to emit at least one beam of electromagnetic rays with wavelengths in the infrared band. In particular, the infrared band refers to the near-infrared to far-infrared band (in particular 0.7 to 1000 μm).

The use of infrared radiation makes it possible to irradiate the person's eyes without dazzling him and, therefore, without him instinctively closing his eyelids. In addition, the use of infrared radiation does not cause pupil constriction that instead visible light does.

Appropriately, according to this embodiment, the optical emitter 3 comprises one or more infrared optical sources 4, for example IR LEDs.

In accordance with a different embodiment, in addition to or as an alternative to infrared radiation, the optical emitter 3 is set up to emit at least one beam of electromagnetic rays with wavelengths in the visible band. For example, the optical emitter comprises one or more optical sources of visible light (e.g., RGB) in addition to or as an alternative to the infrared optical sources 4.

In accordance with a further embodiment, the optical emitter 3 is set up to emit at least one beam of electromagnetic rays with wavelengths in the visible band and at least one beam of electromagnetic rays with wavelengths in the infrared band.

The device 1 in question comprises an electronic processing system 5, which is operatively connected to the optical emitter 3 to switch the latter between an operational state, in which the optical emitter 3 is adapted to project the beam of electromagnetic rays onto the person, and a non-operational state, in which the optical emitter 3 is set up in such a way as not to subject the person to the irradiation of the beam of electromagnetic rays.

In particular, in the operational state the optical emitter 3 (and in particular its light sources 4) is switched on to emit the beam of electromagnetic rays, while in the non-operational state the optical emitter 3 (and in particular its light sources 4) is switched off (its power supply being interrupted, for example).

The electronic processing system 5 is also operatively connected to the optical detector 2 to receive and process the images acquired by the latter.

In accordance with the idea underlying the present invention, the electronic processing system 5 is provided with a face tracking module adapted to identify the position of the face of the person.

In detail, the face tracking module is set up to calculate, from the images acquired by the optical detector 2, a set I of reference points PR indicative of the position of the person's face in the image. In a preferred embodiment, when the optical emitter 3 is set up to emit at least one beam of electromagnetic rays with wavelengths in the visible band and at least one beam of electromagnetic rays with wavelengths in the infrared band, the face tracking module calculates the set I of points on the basis of the images acquired by the optical detector 2 in the infrared band.

In particular, the face tracking module defines a geometric space (preferably three-dimensional) with a reference system in which the coordinates (and therefore the position) of the reference points are identified. Preferably, the three-dimensionality and volume allocation can be approximated using a special software.

Advantageously, the face tracking module is provided with a three-dimensional polygonal mesh modelling algorithm.

For example, the reference points PR calculated by the face tracking module correspond to the vertices of the graphical grid developed through polygonal mesh in order to locate the position of the person's face.

In particular, the face tracking module is adapted to determine the position of the vertices of the grid through an artificial neural network and to treat each vertex as an independent landmark. In particular, the face tracking module associates each reference point PR (landmark) with a three-dimensional coordinate vector that is then mapped into the image.

Figure 5:
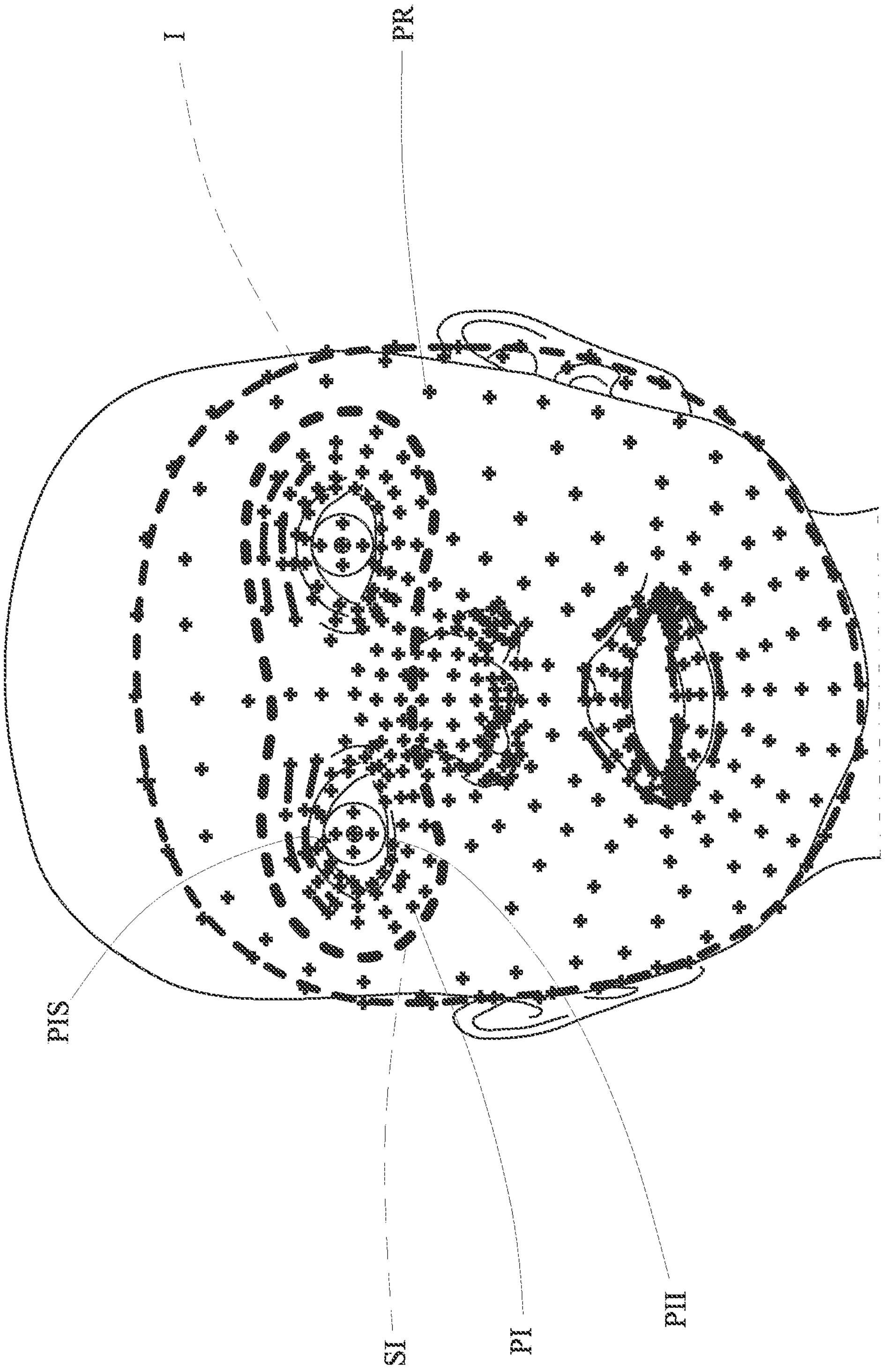
FIG. 5 shows an example of an image to which determined reference points of a person's face have been associated, using the device and the method for detecting the ocular fundus reflex in question.

An example, by way of illustration only, of such mapping is shown in the example of FIG. 5.

The implementation of face tracking modules (in particular of the mesh type) is per se known in the state of the art and will therefore not be described in detail below. Some examples of such algorithms that can be used for this implementation are described in the article "*Real-time Facial Surface Geometry from Monocular Video on Mobile GPUs*" by Kartynnik, Artsiom, Igrishchenko, Grundman.

According to the invention, the electronic processing system 5 comprises an eye state detection module, which is adapted to detect when the person opens his eyes and, consequently, to command the switching on of the optical emitter 3 to obtain the images of the ocular fundus reflex.

More in detail, the detection module is set up to select, in the set I of reference points PR calculated by the face tracking module, a subset SI of points of interest PI relative to the eye area of the face depicted in the image. For example, these points of interest may be indicative of the area of the face between the eyebrow arch and the periocular area of each eye, and in particular the area within the eye contour defined by the eyelids.

The detection module is set up to calculate, as a function of the reciprocal position of the points of interest PI of the aforesaid subset SI, a state parameter PS representative of the degree of eye opening of the face illustrated in the image.

The detection module is therefore set up to compare this state parameter PS with a threshold value VS which is indicative of an open state of the eyes. In particular, the threshold value VS represents a value of the state parameter PS beyond which it is assumed that the eyes of the face depicted in the image are open.

If the state parameter PS is beyond the threshold value VS, the detection module is adapted to switch the optical emitter 3 from the non-operational state into the operational state for a determined time interval IT during which, therefore, the optical emitter 3 projects the beam of electromagnetic radiations onto the person's (open) eyes, so that they produce a beam of reflected rays of the ocular fundus. The radiation beam thus projected onto the person's eyes to produce the beam of reflected rays may be in the same wavelength band as the beam of projected radiations that are used by the face tracking module to calculate the set I of points of interest, or it may advantageously be in a different wavelength band.

By way of example, in a preferred embodiment, when the optical emitter 3 is set up to emit at least one beam of electromagnetic rays with wavelengths in the visible band and at least one beam of electromagnetic rays with wavelengths in the infrared band, when the state parameter PS is beyond the threshold value VS, the optical emitter 3 can advantageously emit the beam of electromagnetic radiations in the visible band onto the (open) eyes of the person, so that they produce a beam of reflected rays of the ocular fundus even if the beam of radiations projected on the patient's face and used by the face tracking module to calculate the set I of points of interest is in the infrared band.

According to this embodiment, the face tracking module can therefore advantageously calculate the set I of points of interest on the basis of images acquired by the optical detector 2 in the infrared band, and the optical detector 2 can acquire analysis images of the person's face containing a beam of reflected rays in the visible band.

In addition, within the aforesaid time interval IT (e.g. 0.5-5 seconds), the optical detector 2 of the device 1 is adapted to acquire analysis images of the face of the person containing the beam of reflected rays of the ocular fundus, so that the latter can be analysed to assess possible abnormalities.

Thus, advantageously, the device 1 in question is able to correctly detect the ocular fundus reflex, in a reliable manner, in particular without the need for the doctor to have to evaluate the moment in which the person (in particular if a newborn) is in the correct position with eyes open for the acquisition of the analysis images of the ocular fundus reflex. In particular, the device 1 in question is capable of reliably acquiring such analysis images in an automated manner without even the need for the presence of a doctor on site.

In addition, the device 1 is capable of switching on the optical emitter 3 only when the person has his eyes open in such a way that the person is subjected to the electromagnetic radiation for a limited period of time (corresponding to the aforesaid time interval IT). In this way, particularly when the beam of electromagnetic rays is in the infrared band, radiation exposure is limited to the shortest possible time, ensuring a high standard of safety for the person. Suitably, in the event that the beam of electromagnetic rays is in the visible band, the short time interval in which the optical emitter 3 is switched on significantly reduces the risk of dazzling the person and thus the person closing his eyes before sufficient analysis images can be acquired.

Advantageously, the detection module of the electronic processing system 5 is set up to calculate the state parameter PS as a function of the distance between the points of interest of the subset SI. If the state parameter PS is greater than the threshold value VS, the detection module commands the optical transmitter 3 to switch from non-operational into operational state.

The detection module is set up to identify, among the points of interest PI of the subset SI, upper points PIS indicative of supraocular areas (in particular of the upper arch of the eye contour) and lower points PII indicative of subocular areas (in particular of the lower arch of the eye contour).

The detection module is then set up to calculate the state parameter PS as a function of the distance between the upper points PIS and the lower points PII of the points of interest PI. Obviously, this distance may be subject to one or more mathematical operations (such as means, weighted means, normalisations, etc.) depending on the specific computational optimisation.

Advantageously, the detection module of the electronic processing system 5 is set up to process the points of interest PI in order to obtain an orientation axis indicative of the direction of the gaze of the person depicted in the image. For example, this orientation parameter can be identified by a direction straight line defined in the geometric space in which the same reference points PR are defined.

The orientation axis (and thus the direction of the gaze of the person in the image) advantageously affects the detection of the ocular fundus reflex obtained by the device and by the method according to the present invention.

The detection module is set up to compare the orientation axis with the optical axis X of the optical detector 2 in order to calculate an angle of deviation, which will be associated with the image.

Preferably, the detection module is set up to command the switching of the optical emitter 3 into the operational state when the aforesaid angle of deviation is less than a determined limit angle indicative of a substantial alignment of the gaze of the person framed with the optical axis X of the optical detector 2.

Preferably, the detection module of the electronic processing system 5 is set up to also process a set of light points PL, i.e. "optical" points of interest, or other light type information, which are generated by the optical sources 4 or by one or more auxiliary optical sources 16, described in more detail below.

Preferably, said light points PL are detected by a module which can be, but is not necessarily, the face tracking module.

By way of example, such light points PL may be information about the brightness of the patient or of his ocular reflexes which, in addition to being useful for measurements and clinical purposes, may be advantageously processed in order to "equalise" images (i.e. to adjust the light intensity of the images), for example by adjusting the intensity of the optical sources. The equalisation of photos is an advantageous and useful aspect to obtain a homogeneous photo dataset, for example for the learning of an artificial intelligence algorithm, for example implemented in the classification module. Appropriately, the optical detector 2 can be set up to frame within its field angle the entire face of the person, or even only a part that in any case allows obtaining sufficient reference points for the execution of the operations discussed above.

Advantageously, the device 1 comprises a support structure 6 on which the optical detector 2, the optical emitter 3 and the electronic processing system 5 are mounted. Said support structure 6 is set up to keep the optical detector 2 and the optical emitter 3 in a determined position at least during their operation.

In accordance with the embodiment illustrated in the accompanying FIGS. 1-4, the support structure 6 comprises a containment body 7, for example box-shaped, inside which the optical detector 2, the optical emitter 3 and the electronic processing system 5 are housed.

Preferably, the containment body 7 comprises a front wall 8, intended to be turned towards the person to be examined, provided with several windows 9 (for example in the form of openings) onto which the optical detector 2 and the optical emitter 3 (and in particular the optical sources 4 of the latter) face.

Referring to the example in FIGS. 3 and 4, the optical sources 4 of the optical emitter 3 are arranged around the camera of the optical detector 2 in a symmetrical manner with respect to the optical axis X of the latter (i.e. in a radial pattern).

Preferably, in accordance with the example of FIG. 1, the support structure 6 comprises a support frame 10, which carries mounted the containment body 7 and is adapted to keep the latter (and therefore the optical emitter 3 and the optical detector 2) in a determined position in front of the person.

For this purpose, the support frame 10 is set up to be secured to a supporting element P. For example, in the application of FIG. 1, the support frame 10 is fixed to the frame of a changing table in order to keep the containment body 7 suspended above the latter in order to capture a child placed inside the changing table itself. In accordance with further embodiments, the support frame 10 may rest on the ground, for example by means of a pedestal or a movable trolley for arranging the device 1 in the place of interest.

Advantageously, the support frame 10 comprises an articulated arm 11, movable by a user to arrange the containment body 7 in a determined position in front of the person.

In accordance with a different application mode, the device 1, during use, may be held directly by the doctor who holds it in front of the person's face. In such a case, in particular, the doctor may directly hold the containment body 7 of the device 1. Appropriately, in order to be able to use the device in both of the above two modes, the containment body 7 is provided with a coupling element 12 by means of which the containment body 7 can be constrained, in a removable manner, to the support frame 10.

Advantageously, the electronic processing system 5 comprises an electronic processor (not visible in the accompanying figures), in particular a microprocessor, arranged within the containment body 7. Preferably, the electronic processor is operatively connected to an electronic controller 13 (also set up within the containment body 7) set up to send command signals to the optical sources 4 of the optical emitter 3 (and appropriately communicate with other electrical/electronic components of the device 1).

Preferably, as illustrated in the example of FIG. 4, the device 1 comprises at least one electrical board 14 (in particular a printed circuit board) on which the optical sources 4 of the optical emitter 3, the optical detector 2 and advantageously the electronic controller 13 of the electronic processing system 5 are mounted.

Suitably, the device 1 comprises a power supply unit electrically connected to the optical emitter 3, the optical detector 2 and the electronic processor 13 (preferably via the electrical board 14) to provide the latter with electrical energy for their operation.

Advantageously, the power supply unit is intended to be connected, by means of an electrical outlet, to an electrical network (it may comprise components, such as a transformer, external or internal to the containment body 7), and/or is provided with a power supply battery mounted in the containment body 7 itself.

Preferably, the face tracking and detection modules of the electronic processing system 5 are implemented by means of one or more software installed in the same hardware device (in particular the electronic processor 13) of the electronic processing system 5 itself. In contrast, the computing modules of the electronic processing system 5 can be obtained by means of separate hardware devices.

In accordance with a further embodiment variant, the electronic processing system 5 (and the relative face tracking and detection modules) can be configured in whole or in part remotely, for example on a server or in the cloud.

Advantageously, the device 1 comprises one or more auxiliary optical sources 16 set up to emit beams of low-intensity rays onto the face of the person.

Such auxiliary optical sources 16 are operatively connected to the electronic processing system 5 (in particular to the microcontroller 13), which is set up to activate them when the optical detector 2 acquires images for the face tracking module, i.e. (also) when the optical emitter 3 is in the non-operational state.

In particular, such auxiliary optical sources 16 are operated by the electronic processing system 5 when the ambient light of the place where the device 1 is operating is not sufficient to allow the optical detector 2 to detect sufficiently sharp images to allow the face tracking module to detect reference points PR on the person's face in the manners discussed above. Such auxiliary optical sources 16 are also advantageously operated by the electronic processing system 5 also to stabilise the brightness conditions by using the light of the device to compensate for ambient brightness, or to stabilise the ocular reflex with respect to the pupil diameter.

For example, such auxiliary light sources 16 may comprise multiple RGB LEDs, or low-energy infrared LEDs.

Advantageously, the electronic processing system 5 comprises a classification module, which is set up to process the representation of the ocular fundus reflex in the analysis images.

These processes are aimed at identifying determined optical characteristics of the reflex image and particular sections thereof, in order to identify any variations or abnormalities with respect to a normal reference image. This allows the classification module to identify the ocular fundus reflex as normal or abnormal, providing a corresponding indication to the doctor who can then decide whether to have the person examined undergo further eye tests. Appropriately, the classification module can be configured to associate different characteristics of the ocular fundus reflex with determined issues or diseases, providing a corresponding indication to the doctor. For example, the variations and abnormalities identified may be associated with an ophthalmological pathology, such as congenital cataract, corneal opacity, retinopathy of prematurity, retinal abnormalities, glaucoma, refractive errors, F.E.V.R. (Familial Exudative Vitreo-Retinopathy), coloboma, uveitis, ocular toxocariasis, Coats' disease, vitreous haemorrhage, retinal dysplasia, refractive errors, or even malignant neoformations of the eye, such as retinoblastoma.

Preferably, the classification module can be implemented by means of an artificial intelligence algorithm based e.g. on a clustering system trained on the basis of several pre-classified cases.

The classification module can thus potentially be implemented to detect various types of issues or pathologies (e.g.

congenital cataract, glaucoma, retinoblastoma, retinal abnormalities, myopia, hypermetropia, etc.), depending on the specific application for which it is intended.

The present invention also relates to a method for detecting the ocular fundus reflex by means of a device (1) comprising:

at least one optical detector (2) set up to detect images, at least one optical emitter (3), which is operable to switch between an operational state, in which said optical emitter (3) emits at least one beam of electromagnetic rays, and a non-operational state;

an electronic processing system (5), which is operatively connected to said optical detector (2) and said optical emitter (3);

wherein said method comprises:

a step of setting up said device (1), wherein said optical detector (2) and said optical emitter (3) are arranged in front of at least a person's face;

a step of acquiring images of the face of said person, wherein said optical detector (2) detects images of the face of said person and sends said images to said electronic processing system (5);

said method being characterized in that it comprises the steps of:

a face tracking step, in which said electronic processing system (5) performs, on said images, a face tracking algorithm, by means of which it calculates a set (I) of reference points (PR) indicative of the position of the person's face in said images;

an eye state detection step, in which said electronic processing system (5):

selects, in said set (I) of reference points (PR), a subset (SI) of points of interest (PI) relative to the eye area of said face in said images;

optionally, selects a set of light points (PL) generated by the optical emitter or by one or more auxiliary optical sources indicative of the ocular reflex of the person in order to adjust the luminous intensity of said images;

identifies, in said subset (SI), upper points (PIS) indicative of supraocular areas and lower points (PII) indicative of subocular areas;

calculates, as a function of the reciprocal position of the points of interest (PI) of said subset (SI), at least one state parameter (PS) representative of the eye opening state of said face in said images, wherein said state parameter (PS) is calculated by said electronic processing system (5) as a function of the distance between said upper points (PIS) and said lower points (PII);

compares said state parameter (PS) with at least a determined threshold value (VS);

if said state parameter (PS) is beyond said threshold value (VS), said method comprises:

a step of activation of said optical emitter (3), wherein said electronic processing system (5) switches said optical emitter (3) into said operational state for a determined time interval (IT), during which said optical emitter (3) projects said at least one beam of electromagnetic rays at least onto the eyes of said person;

wherein as a result of the emission of said at least one beam of electromagnetic rays, the ocular fundus of said person's eyes generates a beam of reflected rays towards said optical detector (2);

during said time interval, an analysis image acquisition step, wherein said optical detector acquires analysis images of said person's face, which analysis images contain said beam of reflected rays of the ocular fundus.

The method according to the present invention can therefore be advantageously carried out by means of the device 1 discussed above, the nomenclature of which introduced so far will be maintained in the following for the sake of simplicity.

Figure 6:
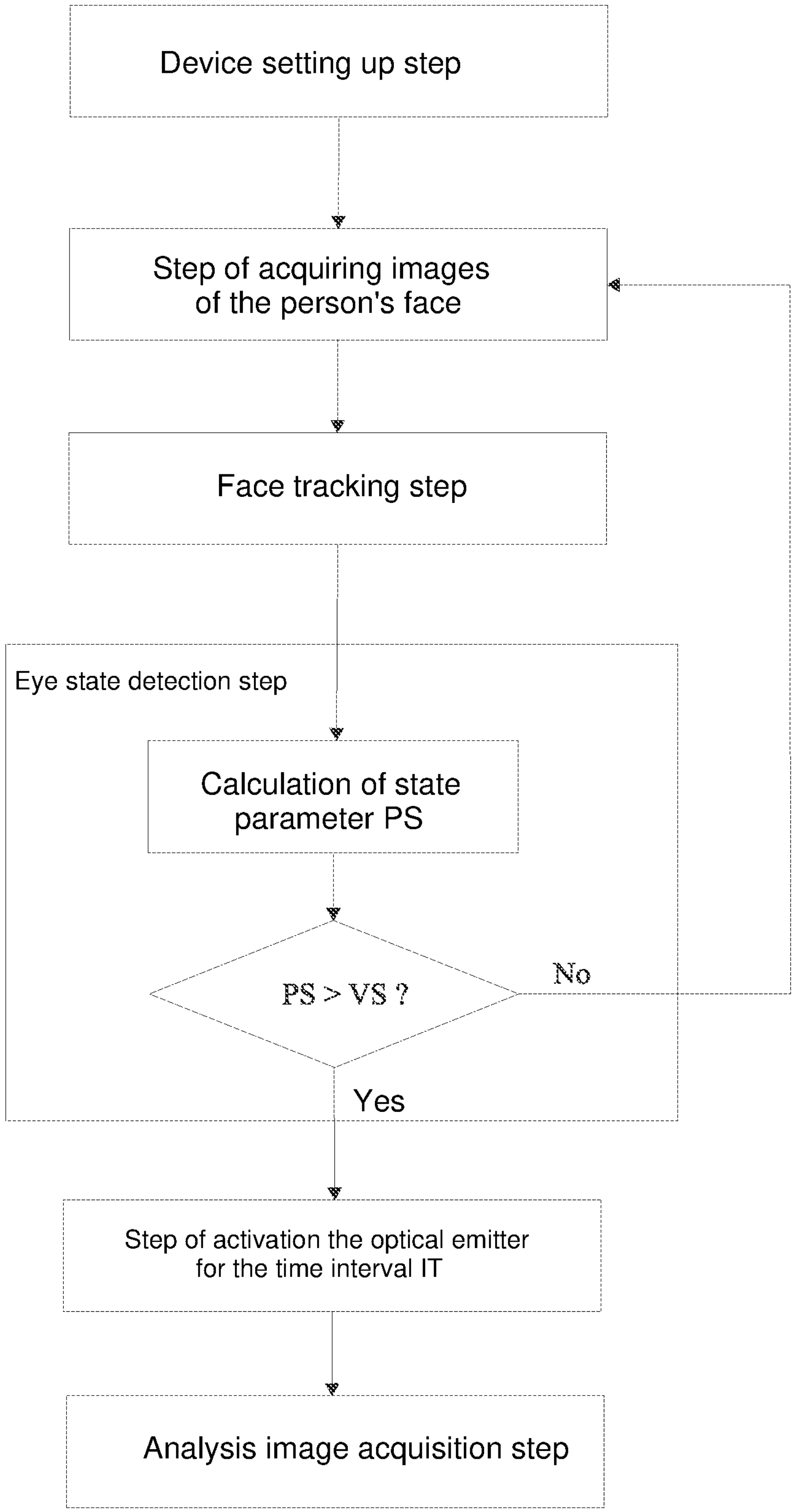
FIG. 6 shows a flowchart of the main operational steps of this method for detecting the ocular fundus reflex in question.

With reference to the diagram of FIG. 6, the method in question comprises a step of setting up the device 1, in which the optical emitter 3 and the optical detector 2 are arranged in front of a person, preferably in front of the face of the person.

Advantageously, the device 1 is positioned in such a way that at least the person's face is within the field angle of the optical detector 2. In particular, following this setting up step, the optical axis X of the optical detector 2 and the projection axis Y of the optical emitter 3 intercept the person, in particular the face of the person.

For example, with reference to the application of FIG. 1, the support frame 6 of the device 1 is set up in such a way that the front wall 8 of the containment body 7 is positioned in front of (in particular above) the area on which the person (in particular the child) is placed, preferably by adjusting the position of the articulated arm 11 of the support frame 10. In accordance with a different application mode, the doctor may position the device 1 in front of the person's face while directly holding the containment body 7 of the device 1 itself.

Advantageously, in order to start the method, the device 1 is switched on, e.g. by the doctor performing the examination.

The method therefore provides for a step of acquiring images of the face of the person, in which the optical detector 2 detects images of the face of the person and sends these images to the electronic processing system 5.

Advantageously, in this acquisition step the optical emitter 3 is in the non-operational state, so that it does not project beams of electromagnetic rays onto the person to be examined.

The images acquired in this acquisition step are processed to identify the position of the face and the state of the eyes and the direction of the gaze or of the head adapted to activate the optical emitter 3 and detect the ocular fundus reflex, as described below.

In accordance with the idea underlying the present invention, the method in question comprises a face tracking step, wherein the electronic processing system 5 performs, on the images received from the optical detector 3, a face tracking algorithm, by means of which it calculates a set of reference points PR indicative of the position of the person's face in the images.

In particular, the face tracking step defines a geometric space (preferably three-dimensional) with a reference system in which the coordinates (and therefore the position) of the reference points are identified, in accordance with what has been discussed above.

Advantageously, the face tracking module is provided with a three-dimensional polygonal mesh modelling algorithm, wherein, for example, the reference points correspond to the vertices of the graphical grid processed by the module to identify the position of the person's face, as discussed above with reference to the operation of the device 1.

The method then includes an eye state detection step to identify when the person opens the eyes in order to perform the ocular fundus reflex detection.

In this detection step, the electronic processing system 5 selects, within the set SI of reference points PR, a subset SI of points of interest PI relative to the eye area of the face in the acquired images. In addition, the electronic processing system 5 calculates, as a function of the reciprocal position of the points of interest PI of the subset SI, a state parameter PS representative of the state of the eyes of the face in the images.

Advantageously, the state parameter PS is calculated as a function of the distance between the points of interest PI of the subset SI.

Advantageously, the state parameter PS is also calculated based on the intensity of the light points PL.

Preferably, in the detection step, the electronic processing system 5 identifies, among the points of interest PI of the subset SI, upper points PIS indicative of supraocular areas (in particular of the upper arch of the eye contour) and lower points PII indicative of points of subocular areas (in particular of the upper arch of the eye contour). The state parameter PS is then calculated as a function of the distance between the upper points PIS and the lower points PII of the points of interest PI. Obviously, this distance may be subject to one or more mathematical operations (such as means, weighted means, normalisations, etc.) depending on the specific computational optimisation.

The electronic processing system 5 compares the state parameter PS with a determined threshold value VS, which is chosen in such a way as to define values of the state parameter PS in which the acquired images depict the face of the person with open eyes.

If the state parameter PS exceeds (and in particular is higher than) the threshold value VS, the method comprises a step of activation of an optical emitter.

In this activation step, the processing electronics system 5 switches the optical emitter 3 from the non-operational state to the operational state and maintains the optical emitter 3 in this operational state for a determined time interval IT. Therefore, in this time interval IT, the optical emitter 3 projects the beam of electromagnetic rays onto the (open) eyes of the person, so that (following irradiation with these beams of electromagnetic rays), the ocular fundus of the eyes generates a beam of reflected rays towards the optical detector 2.

During the aforesaid time interval IT (in which the optical emitter is in the operational state), an analysis image acquisition step is provided, in which the optical detector 2 acquires analysis images of the person's face, which contain a representation of the beam of reflected rays of the ocular fundus that can be used to perform the analysis.

It is noted that the acquisition of analysis images is obtained in an automated manner without the need for medical intervention on the device 1 or on the person. In particular, in the case of the presence of the support structure 6 that keeps the optical emitter 3 and the optical detector 2 in position, the acquisition is also obtained without the need for the doctor to remain on site.

Advantageously, the time interval IT (in which the optical emitter is in the operational state) is substantially between 0.5 and 5 seconds, preferably between 1 and 2 seconds. This time interval IT, depending on the frequency of image acquisition by the optical detector (which can be, for example, 20-30 images per second), makes it possible to acquire a sufficient number of images to reliably acquire the representation of the ocular fundus reflex.

Advantageously, at the end of the time interval IT, the electronic processing system 5 switches the optical emitter 3 from the operational state to the non-operational state.

In particular, the method in question makes it possible to acquire the analysis images by keeping the optical emitter 3 switched on only for the time strictly necessary for detecting the ocular fundus reflex, thus minimising the person's exposure to electromagnetic radiations.

Advantageously, in the detection step the electronic processing system 5 processes the points of interest PI in order to derive an orientation axis indicative of the direction of the gaze of the person depicted in the image and compares this orientation axis with the optical axis X of the optical detector 2 in order to calculate an angle of deviation, which will be associated with the image. Preferably, the electronic processing system 5 commands the switching of the optical emitter 3 into the operational state when the aforesaid angle of deviation is less than a determined limit angle indicative of a substantial alignment of the gaze of the person framed with the optical axis X of the optical detector 2. Advantageously, the electronic processing system 5 also commands said switching according to the light intensity detected by the light points PL. Advantageously, during the image acquisition step, a supplementary illumination step is optionally provided, in which the electronic processing system 5 commands the actuation of the auxiliary optical sources 16 of the device, in order to illuminate the face to be imaged with sufficient light to capture sufficiently sharp images for the execution of the subsequent steps, in case of poor ambient light.

Advantageously, the method in question comprises a classification step in which the electronic processing system 5 processes the representation of the ocular fundus reflex in the analysis images, in order to identify determined optical characteristics of the reflex image and associate them with determined categories, for example to indicate persons who need to undergo in-depth examinations or determined issues or pathology (as discussed above).

In one embodiment of the method, for example, in said classification step the electronic processing system 5 processes the representation of the ocular fundus reflex in the analysis images in order to identify at least one variation or abnormality with respect to a reference image.

Preferably, said classification module implements an artificial intelligence algorithm based on a clustering system trained on the basis of several pre-classified cases.

Preferably, said at least one variation or abnormality is associated with an ophthalmic disease, e.g. congenital cataract, corneal opacity, retinopathy of prematurity, retinal abnormalities, glaucoma, refractive errors, F.E.V.R, coloboma, uveitis, ocular toxocariasis, Coats' disease, vitreous haemorrhage, retinal dysplasia, refractive errors, or even malignant neoformations of the eye, such as retinoblastoma.

The invention thus conceived achieves its intended purpose.

The invention claimed is:

1. Device (1) for detecting the ocular fundus reflex, which comprises:

at least one optical detector (2), which is designed to detect images of a person's face;

at least one optical emitter (3), which is designed to project at least one beam of electromagnetic rays at least onto the eyes of the face of said person, which eyes are likely to generate a beam of reflected rays of the ocular fundus;

an electronic processing system (5), which is operatively connected to said optical detector (2) to receive said images, and is operatively connected to said optical emitter (3) to switch said optical emitter (3) between an operational state, in which said optical emitter (3) is adapted to project said beam of electromagnetic rays onto the face of said person, and a non-operational state; said device (1) being characterized in that said electronic processing system (5) is provided with:

a face tracking module, which is set up to calculate, from said images, a set (I) of reference points (PR) indicative of the position of the person's face in said image;

an eye state detection module, which is set up to:

select, in said set (I) of reference points (PR), a subset (SI) of points of interest (PI) relative to the eye area of the face in said images;

identify, in said subset (SI), upper points (PIS) indicative of supraocular areas and lower points (P11) indicative of subocular areas;

calculate, as a function of the reciprocal position of the points of interest (PI) of said subset (SI), at least one state parameter (PS) representative of the degree of opening of the eyes of the face in said images, wherein said state parameter (PS) is calculated as a function of the distance between said upper points (PIS) and said lower points (P11);

compare said state parameter (PS) with at least one threshold value (VS);-with said state parameter (PS) beyond said threshold value, switch said optical emitter (3) into said operational state for a determined time interval (IT), within which said optical detector (2) is adapted to acquire analysis images containing the beam of reflected rays of the ocular fundus caused by said beam of electromagnetic rays generated by said optical emitter (3).

2. Device (1) according to claim 1, wherein said face tracking module is provided with a three-dimensional polygonal mesh modelling algorithm.

3. Device (1) according to claim 1, wherein said device (1) comprises a support structure (6) which carries mounted said optical detector (2), said optical emitter (3) and said electronic processing system (5), and is designed to maintain said optical detector (2) and said optical emitter (3) in a determined position.

4. Device (1) according to claim 1, wherein said optical emitter (3) is designed to emit said beam of electromagnetic rays with wavelengths in the infrared band.

5. Device (1) according to claim 1, wherein device (1) comprises one or more auxiliary optical sources (16) designed to emit beams of low-intensity light rays at least on the face of said person and operatively connected to said electronic processing system (5), which is designed to activate said auxiliary optical sources (16) when said optical detector (2) acquires said images.

6. Device (1) according to claim 1, wherein said electronic processing system (5) comprises a classification module, which is designed to process the representation of the ocular fundus reflex in the analysis images in order to identify at least one variation or abnormality with respect to a reference image.

7. Device (1) according to claim 6, wherein said classification module is implemented through an artificial intelligence algorithm based on a clustering system trained on the basis of several pre-classified cases.

8. Device (1) according to claim 7, wherein said ophthalmologic pathology is a malignant neoformation of the eye, preferably a retinoblastoma.

9. Device (1) according to claim 6, wherein said at least one variation or abnormality is associated with an ophthalmological pathology.

10. Device (1) according to claim 9, wherein said ophthalmic pathology causing blindness or low vision is selected from the group consisting of: congenital cataract, corneal opacity, retinopathy of prematurity, retinal abnormalities, glaucoma, refractive errors, F.E. V.R., coloboma, uveitis, ocular toxocariasis, Coats' disease, vitreous haemorrhage, retinal dysplasia, refractive errors.

* * * * *